US010360281B2

(12) United States Patent
Pak et al.

(10) Patent No.: US 10,360,281 B2
(45) Date of Patent: Jul. 23, 2019

(54) SYSTEM AND METHOD FOR GENERATING PSEUDO ELECTROGRAM

(71) Applicant: Industry-Academic Cooperation Foundation, Yonsei University, Seoul (KR)

(72) Inventors: Hui Nam Pak, Seoul (KR); Yong Hyeon Yun, Seoul (KR)

(73) Assignee: Industry-Academic Cooperation Foundation, Yonsei University, Gyeonggi-do (KR)

( * ) Notice: Subject to any disclaimer, the term of this patent is extended or adjusted under 35 U.S.C. 154(b) by 453 days.

(21) Appl. No.: 14/426,400

(22) PCT Filed: Sep. 6, 2013

(86) PCT No.: PCT/KR2013/008057
§ 371 (c)(1),
(2) Date: Mar. 6, 2015

(87) PCT Pub. No.: WO2014/038883
PCT Pub. Date: Mar. 13, 2014

(65) Prior Publication Data
US 2015/0242587 A1 Aug. 27, 2015

(30) Foreign Application Priority Data
Sep. 7, 2012 (KR) .................. 10-2012-0099076

(51) Int. Cl.
*G06F 17/11* (2006.01)
*G06F 17/50* (2006.01)
(Continued)

(52) U.S. Cl.
CPC .......... *G06F 17/11* (2013.01); *A61B 5/04021* (2013.01); *A61B 5/7278* (2013.01);
(Continued)

(58) Field of Classification Search
USPC ............ 703/2, 17; 600/509, 479; 607/18, 25
See application file for complete search history.

(56) References Cited

U.S. PATENT DOCUMENTS 4,585,004 A * 4/1986 Brownlee ............ A61B 5/0031
128/903
5,111,816 A * 5/1992 Pless .................... A61N 1/3622
607/4
(Continued)

FOREIGN PATENT DOCUMENTS

KR 10-2007-0075347 A 7/2007
KR 10-2009-0056871 A 6/2009
(Continued)

OTHER PUBLICATIONS

European Patent Office, Supplementary European Search Report dated May 4, 2016 against the corresponding European Application No. 13834431.
(Continued)

*Primary Examiner* — Thai Q Phan
(74) *Attorney, Agent, or Firm* — Hammer & Associates, P.C.

(57) ABSTRACT

Provided are a system and method for generating a pseudo electrogram. The system for generating the pseudo electrogram includes a unipolar electrogram generation unit which generates a unipolar electrogram according to an action potential calculated from an electric physiological model of the heart using a pseudo electrode in which a cross-sectional area is adjusted, and a pseudo electrogram generation unit which generates a pseudo electrogram using the unipolar electrogram.

6 Claims, 9 Drawing Sheets

(51) Int. Cl.
*A61B 5/0402* (2006.01)
*A61B 5/00* (2006.01)
*G16H 50/50* (2018.01)
*G06F 19/00* (2018.01)
*A61N 1/365* (2006.01)

(52) U.S. Cl.
CPC ............ *G06F 19/00* (2013.01); *G16H 50/50* (2018.01); *A61N 1/365* (2013.01)

(56) References Cited

U.S. PATENT DOCUMENTS

| | | | |
|---|---|---|---|
| 5,692,907 | A | 12/1997 | Glassel et al. |
| 6,772,004 | B2 * | 8/2004 | Rudy .................. A61B 5/0422 600/411 |
| 8,718,750 | B2 * | 5/2014 | Lian .................... A61N 1/3627 600/509 |
| 2002/0128565 | A1 * | 9/2002 | Rudy .................. A61B 5/0422 600/509 |
| 2005/0202384 | A1 | 9/2005 | Dicuccio et al. |
| 2008/0109041 | A1 * | 5/2008 | de Voir ............. A61B 5/04017 607/7 |
| 2012/0302904 | A1 * | 11/2012 | Lian .................... A61N 1/3627 600/509 |
| 2013/0079645 | A1 * | 3/2013 | Amirana ............. A61B 5/0084 600/479 |
| 2016/0331471 | A1 * | 11/2016 | Deno .................... A61B 34/20 |

FOREIGN PATENT DOCUMENTS

| | | |
|---|---|---|
| KR | 10-2011-0082038 A | 7/2011 |
| WO | WO 2010/042826 A1 | 4/2010 |

OTHER PUBLICATIONS

D.D.Correa De Sa et al., "Electrogram Fractionation: The Relationship Between Spatiotemporal Variation of Tissue Excitation and Electrode Spatial Resolution", Circulation. Arrhythmia and Electrophysiology, vol. 4, No. 6, US, Dec. 23, 2011, pp. 909-916.
Kneller, J. et al., "Cholinergic Atrial Fibrillation in a Computer Model of a Two-Dimensional Sheet of Canine Atrial Cells With Realistic Ionic Properties", Circulation Research, vol. 90, No. 9, May 17, 2002, pp. 73e-87.
Elvan, A. et al., "Dominant Frequency of Atrial Fibrillation Correlates Poorly With Atrial Fibrillation Cycle Length", Circulation, Arrhythmia and Electrophysiology, US, vol. 2, No. 6, Oct. 19, 2009, pp. 634-644.
Mark Potse, "Mathematical Modeling and Simulation of Ventricular Activation Sequences: Implications for Cardiac Resynchronization Therapy", Journal of Cardiovascular Translational Research, Springer US, Boston, vol. 5, No. 2, Jan. 27, 2012, pp. 146-158.

* cited by examiner

SYSTEM AND METHOD FOR GENERATING PSEUDO ELECTROGRAM

CROSS-REFERENCE TO RELATED APPLICATION

This application claims priority to and the benefit of Korean Patent Application No. 2012-0099076, filed on Sep. 7, 2012, the disclosure of which is incorporated herein by reference in its entirety.

BACKGROUND

1. Field of the Invention

The present invention relates to a system and method for generating a pseudo electrogram, and more particularly, to a system and method for generating a pseudo electrogram for use in generation of a complex fractionated atrial electrogram (CFAE).

2. Discussion of Related Art

Cardiac arrhythmia is a rhythm disease of the heart in which the pulse is slower or faster than normal, or is irregular. Atrial fibrillation is a very common type of cardiac arrhythmia and is a refractory disease, and it is estimated that about 1.6% of the population in Korea has the atrial fibrillation. The atrial fibrillation is a disease in which older people, especially 60 years old or more, are affected, and it has increased in younger people recently, and is not uncommon in cases which have a common family history.

Another characteristic of the atrial fibrillation is that the case of not feeling symptoms reaches to about 20%. However, in the case of the atrial fibrillation, since the risk of an ischemic stroke (a cerebral infarction) is in a range of 5% to 10% per year (in a range of 15% to 20% of total cerebral infarction patients), people without symptoms break down sometimes due to the stroke which is complicated by the atrial fibrillation. As such, the atrial fibrillation is also an intractable arrhythmia that is difficult to treat as well as is often delayed in diagnosing. However, it is possible to fundamentally treat the atrial fibrillation due to developments of recent advanced medical technologies, and a treatment success rate is also greatly increasing.

Treatments of the atrial fibrillation may be largely divided into three categories. The first is an antithrombotic therapy which prevents the strokes, the second is a therapy which relieves symptoms by adjusting the pulse so as not to accelerate, and the third is a fundamental therapy which eliminates the atrial fibrillation and maintains a normal pulse. A treatment developed to overcome the low efficiency and the risk of adverse effects of antiarrhythmic drugs as a fundamental therapy is called radiofrequency catheter ablation. The radiofrequency catheter ablation is a treatment developed so as to simplify the maze surgery which is originally used when heart surgeons perform heart valve surgeries. It is a treatment in which a thin electrode having a 3.5 mm diameter is inserted into a leg blood vessel and reaches the heart without incisions or general anesthesia, burns the tissues with radiofrequency energy or damages the tissues using cryotherapy, and thus fundamentally eliminates areas in which the atrial fibrillation appears. Since it is a very precise treatment, it takes about four hours to perform the treatment, and, there are advantages in which recovery thereof is faster than that of the case of performing surgery and it is possible to perform normal activities on the day after the treatment. The radiofrequency catheter ablation has a recurrence rate, however, a cure rate of paroxysmal atrial fibrillation grows in a range of 85% to 90%, and it is possible to completely cure persistent atrial fibrillation in a range of 70% to 75%.

The radiofrequency catheter ablation for the treatment of the cardiac arrhythmias is a method of performing a treatment so that electrical activities of the heart can be normally achieved by damaging the patient's heart tissues, however, there is a problem in that it is difficult to revive the damaged heart tissues. Therefore, an area in which the radiofrequency catheter ablation will be performed should be very carefully selected, and there is plenty of room for improvement in a mapping method and an ablation method.

SUMMARY OF THE INVENTION

The present invention is directed to a system and method for generating a pseudo electrogram in which an electrogram for inducing a complex fractionated atrial electrogram is non-invasively generated using a pseudo electrode, and location data for performing radiofrequency catheter ablation is provided through the electrogram, electrical physiological activities found in the heart of a patient during surgery are predicted, and then a result of the prediction is predicted and diagnosed.

According to an aspect of the present invention, there is provided a system for generating a pseudo electrogram, including: a unipolar electrogram generation unit which generates a unipolar electrogram according to an action potential calculated from an electric physiological model of the heart using a pseudo electrode of which a cross-sectional area is adjusted; and a pseudo electrogram generation unit which generates a pseudo electrogram using the unipolar electrogram.

The pseudo electrode may include a first electrode and a second electrode.

The unipolar electrogram generation unit may generate the unipolar electrogram according to the following equation.

$$V = \frac{S_2}{S_1} \times \sum_{x=x_0}^{x_0+k-1} \sum_{y=y_0}^{y_0+l-1} V(x, y)$$

($S_1$: a cross-sectional area of an electrode, $S_2$: a cross-sectional area of a unit cell, $x_0$: a location of a tip of a pseudo electrode on an x-axis, k: the number of cells occupied by the electrode on the x-axis, $y_0$: a location of a tip of a pseudo electrode on a y-axis, l: the number of cells occupied by the electrode on the y-axis, V: an action potential)

The pseudo electrogram generation unit may calculate the pseudo electrogram using a difference between a unipolar electrogram of the first electrode and a unipolar electrogram of the second electrode.

The system may further include a filtering unit which filters only a signal in a predetermined frequency range from the pseudo electrogram.

The filtering unit may filter only a signal in a frequency range of 30 Hz to 300 Hz.

According to another aspect of the present invention, there is provided a method for generating a pseudo electrogram, including: generating a unipolar electrogram according to an action potential calculated from an electric physiological model of the heart using a pseudo electrode in which a cross-sectional area is adjusted; and generating a pseudo electrogram using the unipolar electrogram.

The generating of the unipolar electrogram may generate the unipolar electrogram according to the following equation.

$$V = \frac{S_2}{S_1} \times \sum_{x=x_0}^{x_0+k-1} \sum_{y=y_0}^{y_0+l-1} V(x, y)$$

($S_1$: a cross-sectional area of an electrode, $S_2$: a cross-sectional area of a unit cell, $x_0$: a location of a tip of a pseudo electrode on an x-axis, k: the number of cells occupied by the electrode on the x-axis, $y_0$: a location of a tip of a pseudo electrode on a y-axis, l: the number of cells occupied by the electrode on the y-axis, V: an action potential)

The generating of the pseudo electrogram may calculate the pseudo electrogram using a difference between a unipolar electrogram of a first electrode and a unipolar electrogram of a second electrode.

BRIEF DESCRIPTION OF THE DRAWINGS

The above and other objects, features and advantages of the present invention will become more apparent to those of ordinary skill in the art by describing in detail exemplary embodiments thereof with reference to the accompanying drawings, in which.

DETAILED DESCRIPTION OF EXEMPLARY EMBODIMENTS

Figure 1:
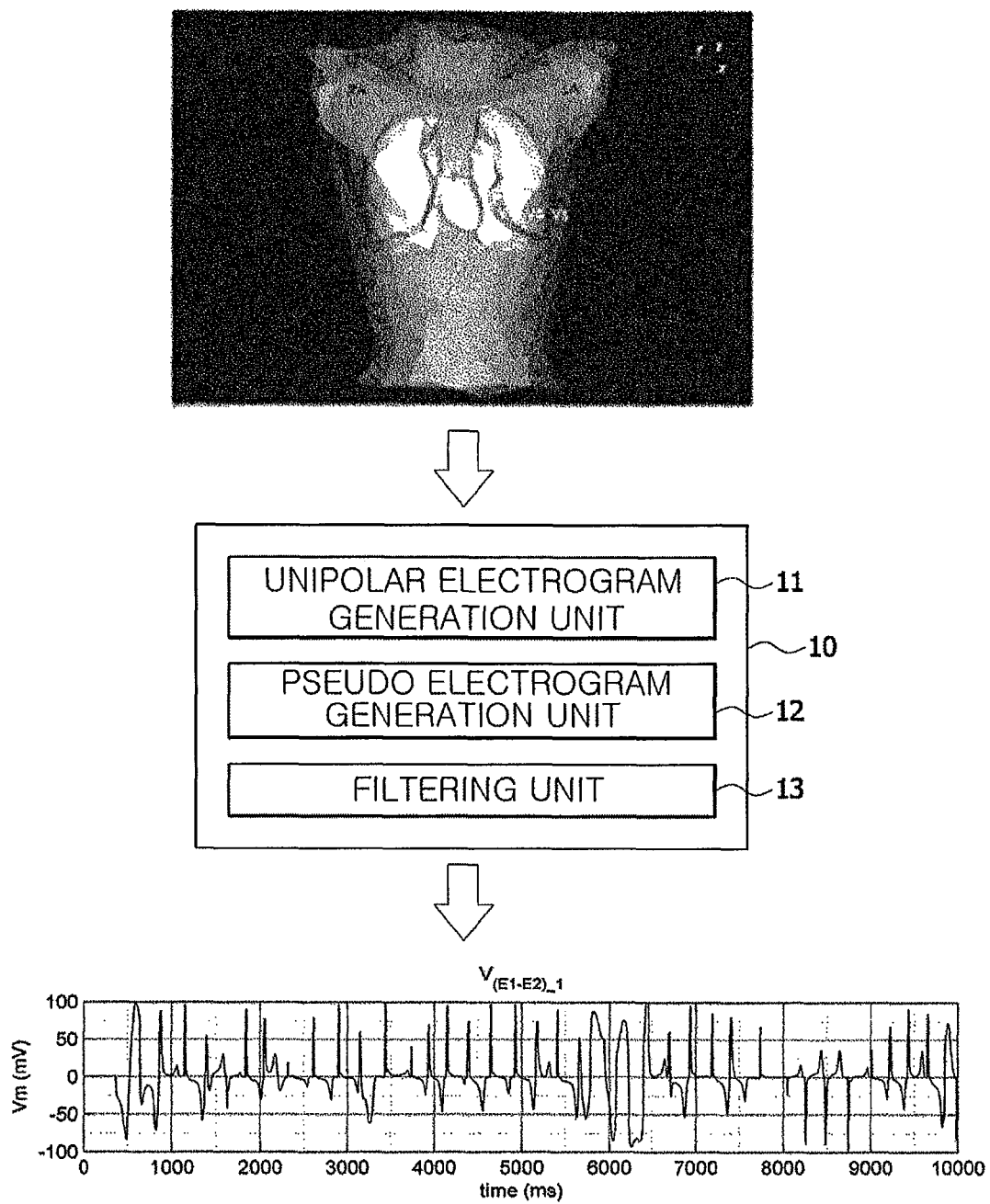
FIG. 1 is a schematic view of a system for generating a pseudo electrogram according to an exemplary embodiment of the present invention.

While the invention is susceptible to various modifications and alternative forms, specific embodiments thereof are shown by way of example in the drawings and will herein be described in detail. It should be understood, however, that there is no intent to limit the invention to the particular forms disclosed, but on the contrary, the invention is to cover all modifications, equivalents, and alternatives falling within the spirit and scope of the invention.

It will be understood that, although the terms "first," "second," etc. may be used herein to describe various elements, these elements should not be limited by these terms. These terms are only used to distinguish one element from another. For example, a second element could be termed a first element, and, similarly, a first element could be termed a second element, without departing from the scope of the present invention. As used herein, the term "and/or" includes any and all combinations of one or more of the associated listed items.

It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

The terminology used herein is for the purpose of describing particular embodiments only and is not intended to be limiting of the invention. As used herein, the singular forms "a," "an," and "the" are intended to include the plural forms as well, unless the context clearly indicates otherwise. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Hereinafter, exemplary embodiments of the invention will be described in detail with reference to the accompanying drawings. In order to facilitate overall understanding of the invention, like reference numerals in the drawings denote like elements, and thus the description thereof will not be repeated.

Figure 2:
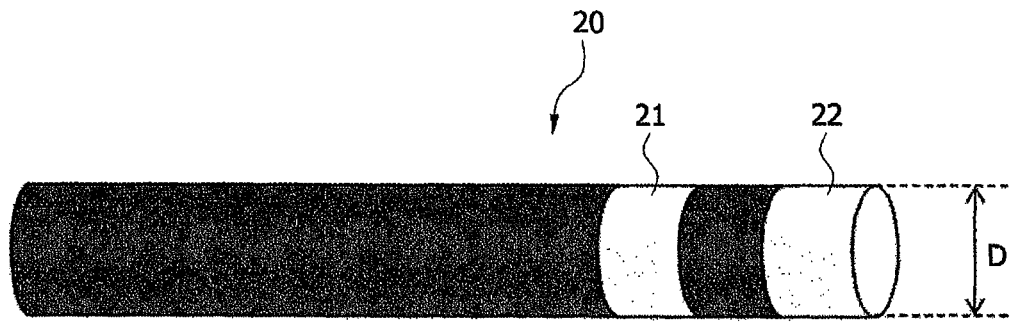
FIG. 2 is a conceptual view of a pseudo electrode according to an exemplary embodiment of the present invention.
Figure 3:
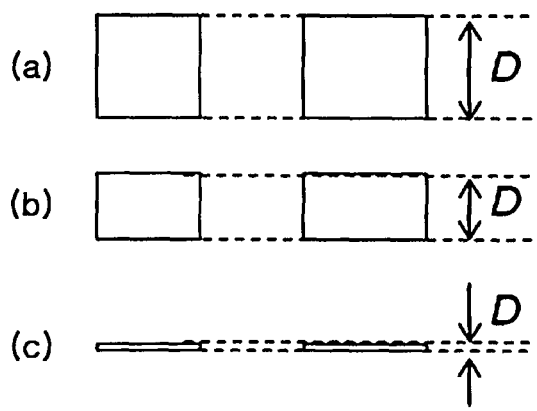
FIG. 3 is a conceptual view of a size of a cross-sectional area of a pseudo electrode according to an exemplary embodiment of the present invention.

FIG. 1 is a schematic view of a system for generating a pseudo electrogram according to an exemplary embodiment of the present invention, FIG. 2 is a conceptual view of a pseudo electrode according to the exemplary embodiment of the present invention, and FIG. 3 is a conceptual view of a size of a cross-sectional area of the pseudo electrode according to the exemplary embodiment of the present invention.

Referring to FIG. 1, the system for generating the pseudo electrogram according to the exemplary embodiment of the present invention may include a unipolar electrogram generation unit 11 which generates a unipolar electrogram according to an action potential calculated from an electric physiological model of the heart using a pseudo electrode in which a cross-sectional area is adjusted according to a contact state, a pseudo electrogram generation unit 12 which generates a pseudo electrogram using the unipolar electrogram, and a filtering unit 13 which filters only signals in a predetermined frequency range from the pseudo electrogram.

Referring to FIG. 2, the pseudo electrode according to the exemplary embodiment of the present invention may include a first electrode 21 and a second electrode 22.

A cross-sectional area D of the pseudo electrode may be arbitrarily adjusted according to a contact state of an electrode. Referring to FIG. 3, the cross-sectional area D of the pseudo electrode may be divided into three cases. The case of (a) shows a case in which the electrode contact state of the pseudo electrode is good, and in this case, it is preferable that the cross-sectional area D of the electrode is most largely adjusted. The case of (b) shows a case in which the electrode contact state of the pseudo electrode is normal, and in this case, it is preferable that the cross-sectional area D of the electrode is set to be in an intermediate operation. The case of (c) shows a case in which the electrode contact state of the pseudo electrode is not good, and in this case, it is preferable that the cross-sectional area D of the electrode is minimally set. The cross-sectional area D of the pseudo electrode may be adjusted by the external setting.

The unipolar electrogram generation unit 11 may generate a unipolar electrogram according to an action potential calculated from an electric physiological model of the heart using the pseudo electrode in which the cross-sectional area is adjusted according to the contact state.

A method of calculating the action potential from the electric physiological model of the heart, for example, may use a ventricular cell model using the tenTusscher model, and an atrial model, which is based on the DiFrancesco and Noble models and uses the Nygren model partially made up of an LMCG model. The method of calculating the action potential from the electric physiological model of the heart may use other well-known techniques in addition to the above-described method, and detailed descriptions thereof will be omitted because it may obscure the gist of the invention.

The unipolar electrogram generation unit 11 may generate the unipolar electrogram according to the following equation.

$$V = \frac{S_2}{S_1} \times \sum_{x=x_0}^{x_0+k-1} \sum_{y=y_0}^{y_0+l-1} V(x, y)$$

($S_1$: a cross-sectional area of an electrode, $S_2$: a cross-sectional area of a unit cell, $x_0$: a location of a tip of a pseudo electrode on an x-axis, k: the number of cells occupied by the electrode on the x-axis, $y_0$: a location of a tip of a pseudo electrode on a y-axis, l: the number of cells occupied by the electrode on the y-axis, V: an action potential)

Hereinafter, a process of generating the unipolar electrogram according to the electrode contact state of the pseudo electrode will be described with reference to FIGS. 4 to 12.

Figure 4:
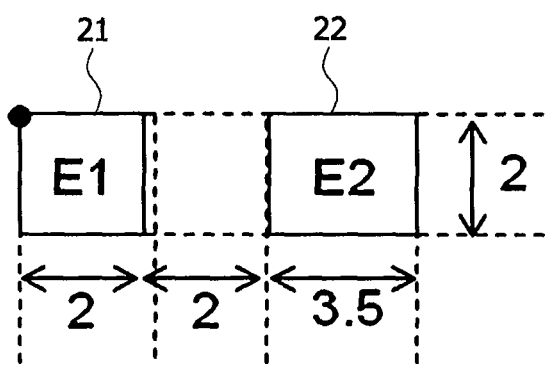
FIG. 4 is a view showing settings of a cross-sectional area of a pseudo electrode according to an exemplary embodiment of the present invention.
Figure 5:
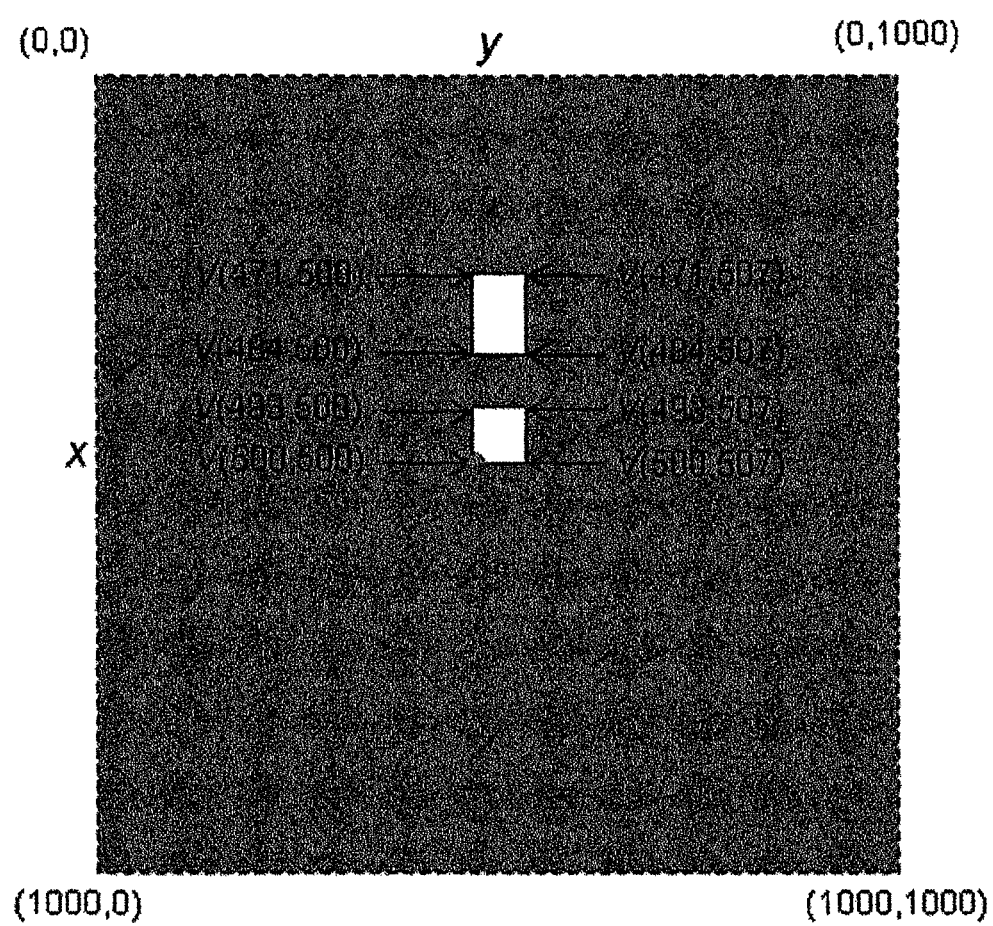
FIG. 5 is a view showing an arrangement of the pseudo electrode according to the exemplary embodiment of the present invention.
Figure 6:
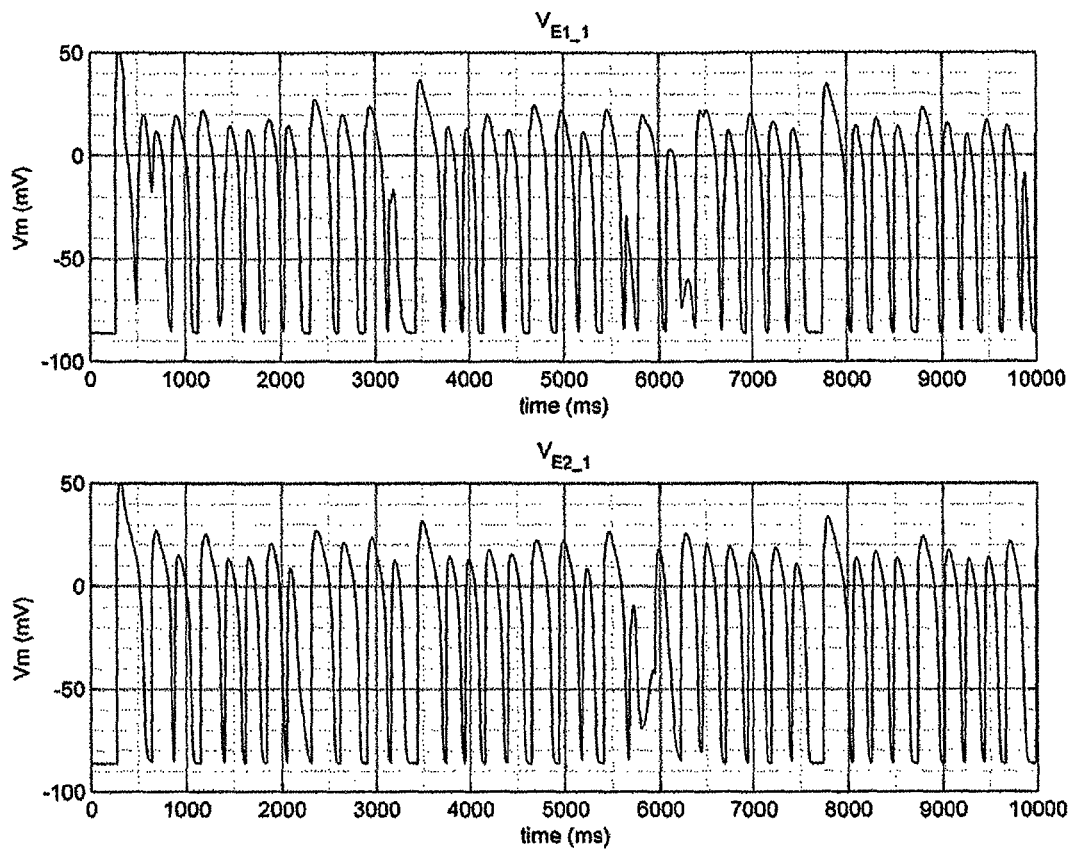
FIG. 6 shows unipolar electrograms according to the exemplary embodiment of the present invention.

FIG. 4 is a view showing settings of a cross-sectional area of a pseudo electrode according to an exemplary embodiment of the present invention, FIG. 5 is a view showing an arrangement of the pseudo electrode according to the exemplary embodiment of the present invention, and FIG. 6 shows unipolar electrograms according to the exemplary embodiment of the present invention.

In the exemplary embodiment of the present invention, when the electrode contact state of the pseudo electrode is good, the cross-sectional area of the pseudo electrode is set to 2 mm, and a length of the first electrode 21 and a length of the second electrode 22 are set to 2 mm and 3.5 mm, respectively. An area of the heart for generating the pseudo electrogram using the pseudo electrode is 25×25 (cm$^2$), an area of a unit cell is 0.25×0.25 (mm$^2$), and thus 1000×1000 unit cells may be distributed.

Referring to FIG. 5, when one corner of the first electrode 21 is located at a point (500, 500) and a tip electrode of the pseudo electrode is located thereover, a unipolar electrogram of the first electrode 21 may be calculated according to $$V_{E1\_1} = \frac{1}{64} \sum_{x=493}^{500} \sum_{y=500}^{507} V(x, y)$$

and a unipolar electrogram of the second electrode 22 may be calculated according to $$V_{E2\_1} = \frac{1}{112} \sum_{x=471}^{484} \sum_{y=500}^{507} V(x, y)$$

by the unipolar electrogram generation unit 11.

As shown in FIG. 6, the unipolar electrograms may be generated through the above-described process.

Figure 7:
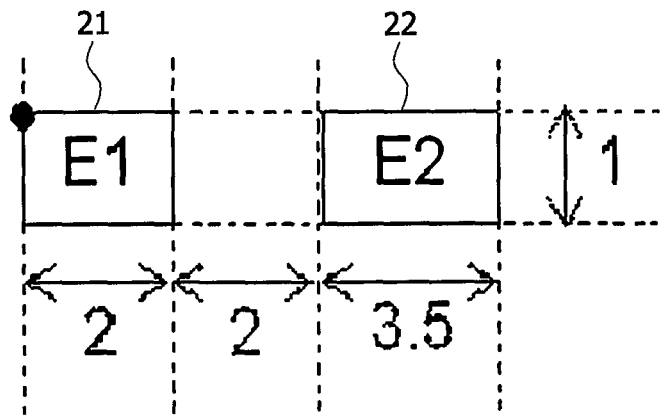
FIG. 7 is a view showing settings of a cross-sectional area of a pseudo electrode according to another exemplary embodiment of the present invention.
Figure 8:
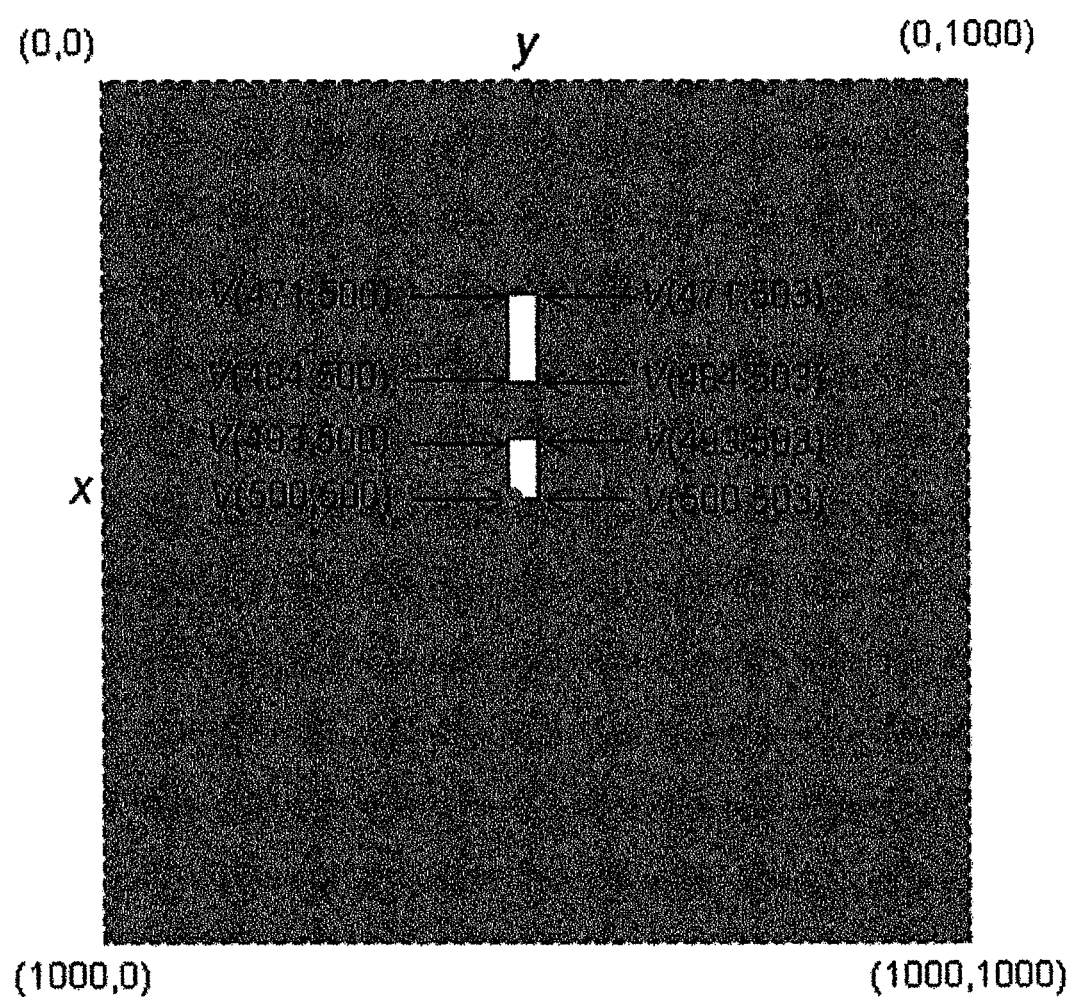
FIG. 8 is a view showing an arrangement of the pseudo electrode according to the exemplary embodiment of the present invention.
Figure 9:
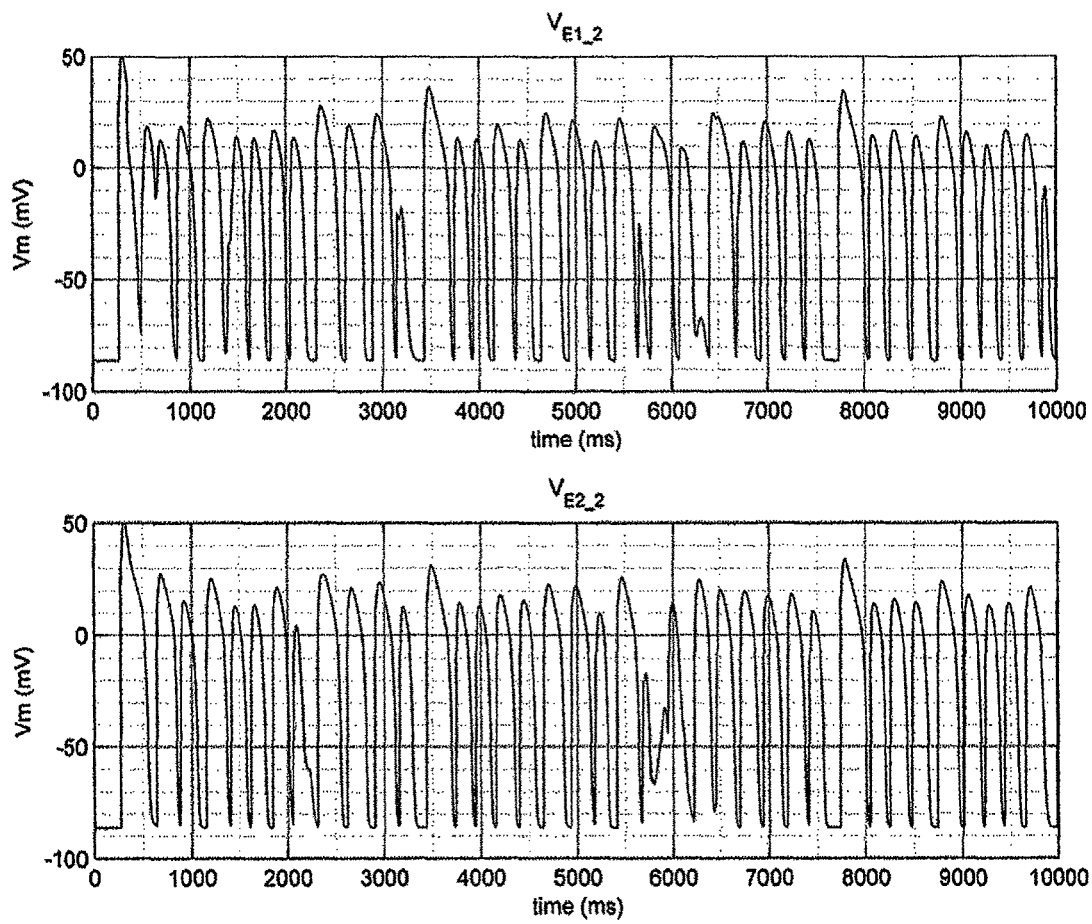
FIG. 9 shows unipolar electrograms according to the exemplary embodiment of the present invention.

FIG. 7 is a view showing settings of a cross-sectional area of a pseudo electrode according to another exemplary embodiment of the present invention, FIG. 8 is a view showing an arrangement of the pseudo electrode according to the exemplary embodiment of the present invention, and FIG. 9 shows unipolar electrograms according to the exemplary embodiment of the present invention.

In the exemplary embodiment of the present invention, when the electrode contact state of the pseudo electrode is normal, the cross-sectional area of the pseudo electrode is set to 1 mm, and a length of the first electrode 21 and a length of the second electrode 22 are set to 2 mm and 3.5 mm, respectively. An area of the heart for generating the pseudo electrogram using the pseudo electrode is 25×25 (cm$^2$), an area of the unit cell is 0.25×0.25 (mm$^2$), and thus 1000×1000 unit cells may be distributed.

Referring to FIG. 8, when one corner of the first electrode 21 is located at a point (500, 500) and a tip electrode of the pseudo electrode is located thereover, a unipolar electrogram of the first electrode 21 may be calculated according $$V_{E1\_2} = \frac{1}{32} \sum_{x=493}^{500} \sum_{y=500}^{503} V(x, y)$$

to and a unipolar electrogram of the second electrode 22 may be calculated according to $$V_{E2\_2} = \frac{1}{56} \sum_{x=471}^{484} \sum_{y=500}^{503} V(x, y)$$

by the unipolar electrogram generation unit 11.

As shown in FIG. 9, the unipolar electrograms may be generated through the above-described process.

Figure 10:
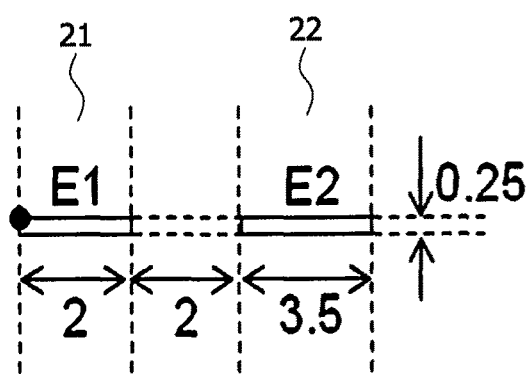
FIG. 10 is a view showing settings of a cross-sectional area of a pseudo electrode according to still another exemplary embodiment of the present invention.
Figure 11:
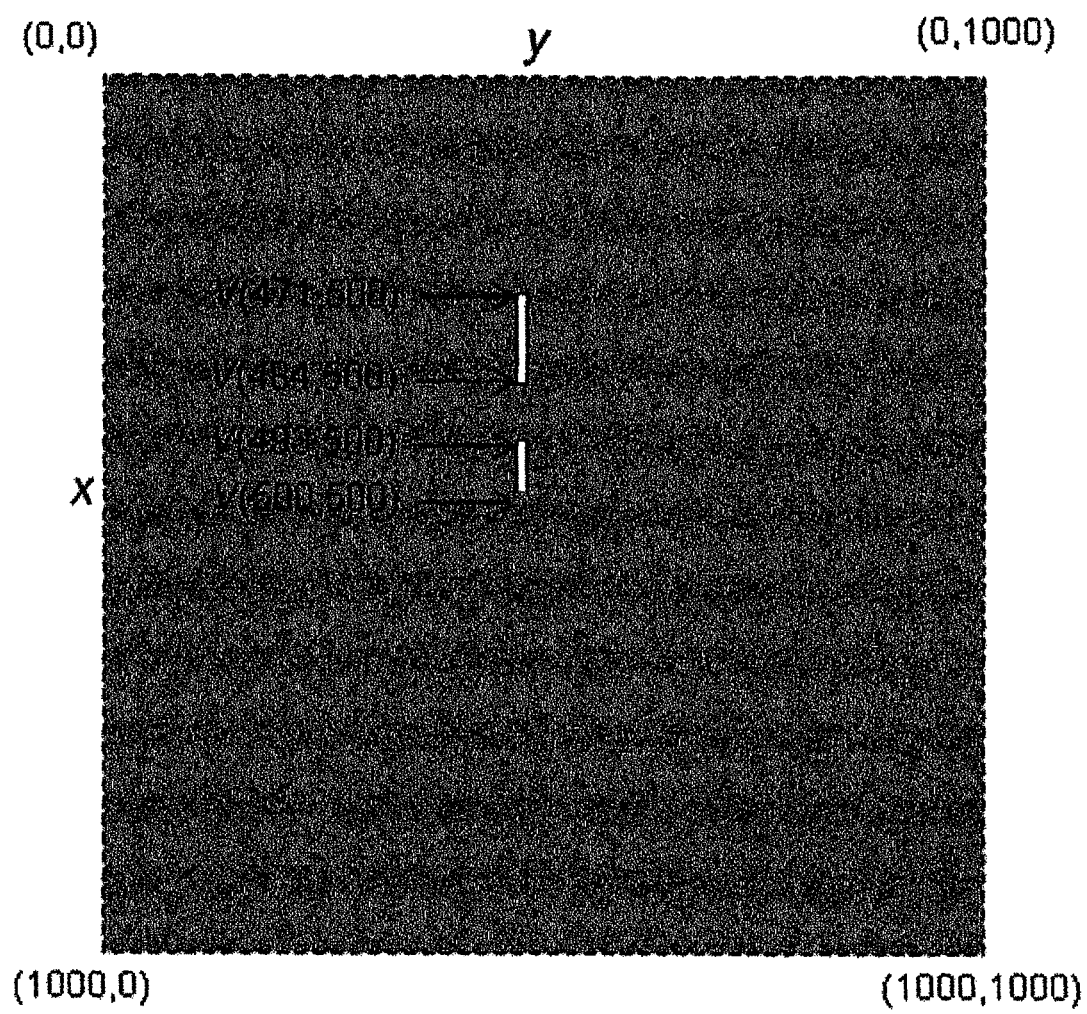
FIG. 11 is a view showing an arrangement of the pseudo electrode according to the exemplary embodiment of the present invention.
Figure 12:
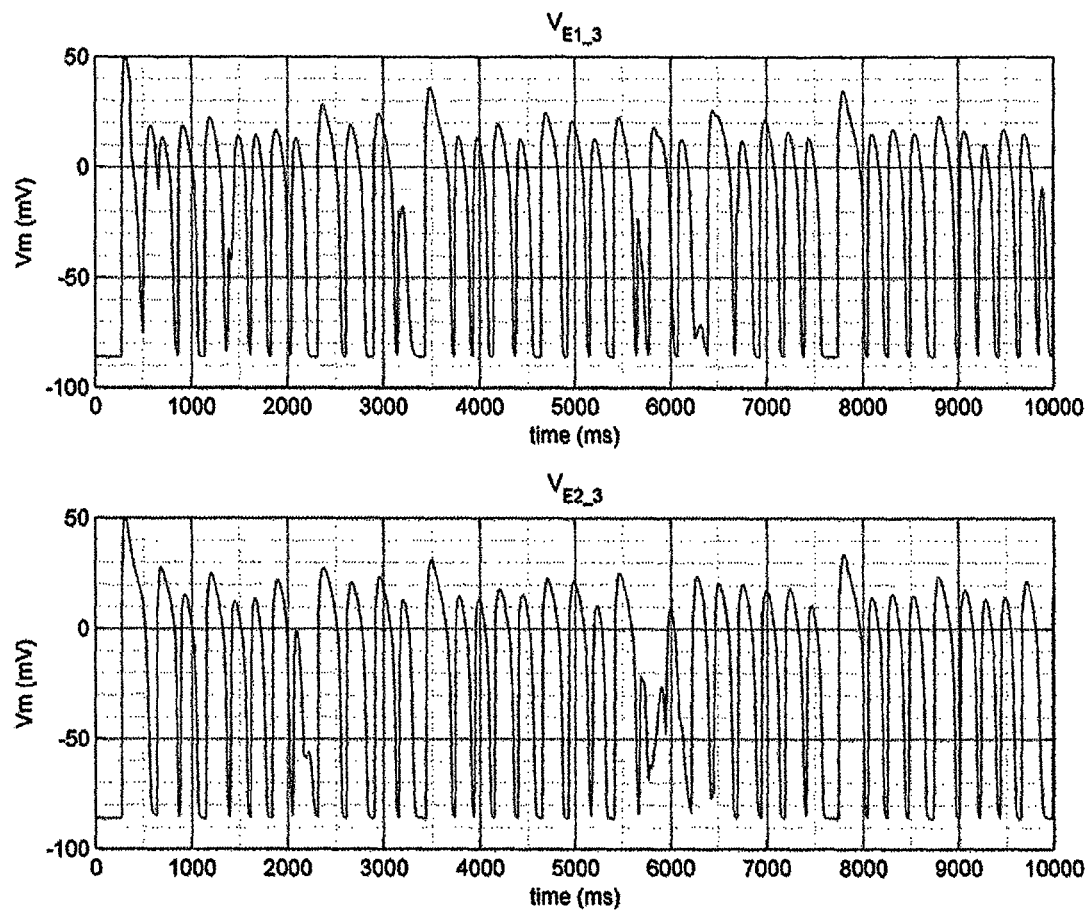
FIG. 12 shows unipolar electrograms according to the exemplary embodiment of the present invention.

FIG. 10 is a view showing settings of a cross-sectional area of a pseudo electrode according to still another exemplary embodiment of the present invention, FIG. 11 is a view showing an arrangement of the pseudo electrode according to the exemplary embodiment of the present invention, and FIG. 12 shows unipolar electrograms according to the exemplary embodiment of the present invention.

In the exemplary embodiment of the present invention, when the electrode contact state of the pseudo electrode is not good, the cross-sectional area of the pseudo electrode is set to 0.25 mm, and a length of the first electrode 21 and a length of the second electrode 22 are set to 2 mm and 3.5 mm, respectively. An area of the heart for generating the pseudo electrogram using the pseudo electrode is 25×25 (cm$^2$), an area of the unit cell is 0.25×0.25 (mm$^2$), and thus 1000×1000 unit cells may be distributed.

Referring to FIG. 11, when one corner of the first electrode 21 is located at a point (500, 500) and a tip electrode of the pseudo electrode is located thereover, a unipolar electrogram of the first electrode 21 may be calculated according to $$V_{E1\_3} = \frac{1}{8} \sum_{x=493}^{500} V(x, 500)$$

and a unipolar electrogram of the second electrode 22 may be calculated according to $$V_{E2\_3} = \frac{1}{14} \sum_{x=471}^{484} V(x, 500)$$

by the unipolar electrogram generation unit 11.

As shown in FIG. 12, the unipolar electrograms may be generated through the above-described process.

The pseudo electrogram generation unit 12 may calculate the pseudo electrogram using a difference between the unipolar electrogram of the first electrode 21 and the unipolar electrogram of the second electrode 22.

An example of the process of generating the pseudo electrogram will be described using the unipolar electrograms generated through the processes shown in FIGS. 4 to 12.

Figure 13:
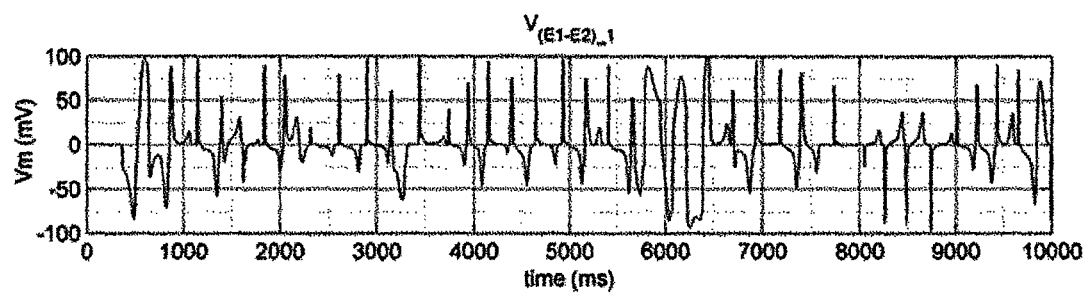
FIG. 13 is a pseudo electrogram generated according to an exemplary embodiment of the present invention.

FIG. 13 is a pseudo electrogram generated according to an exemplary embodiment of the present invention. According to the exemplary embodiment of the present invention, the pseudo electrogram generation unit 12 may calculate the pseudo electrogram using Equation (2) through a difference between a first unipolar electrogram and a second unipolar electrogram which are calculated when an electrode contact state of the pseudo electrode is good.

$$V_{(E1-E2)\_1} = V_{E1\_1} - V_{E2\_1} = \frac{1}{64} \sum_{x=493}^{500} \sum_{y=500}^{507} V(x, y) - \frac{1}{112} \sum_{x=471}^{484} \sum_{y=500}^{507} V(x, y) \quad \text{Equation (2)}$$

Figure 14:
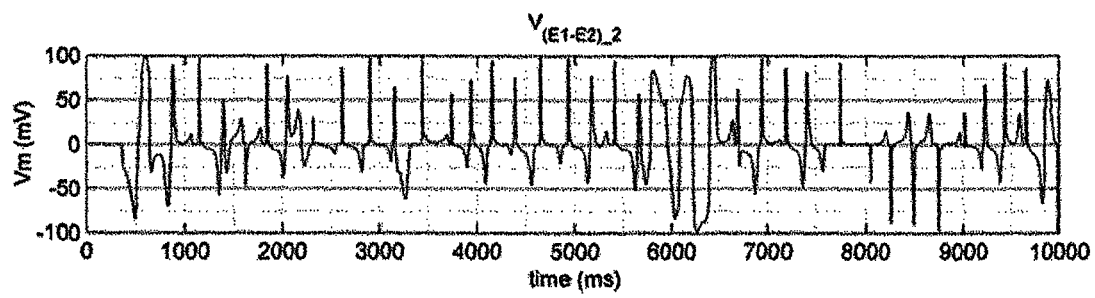
FIG. 14 is a pseudo electrogram generated according to another exemplary embodiment of the present invention.

FIG. 14 is a pseudo electrogram generated according to another exemplary embodiment of the present invention. According to the exemplary embodiment of the present invention, the pseudo electrogram generation unit 12 may calculate the pseudo electrogram using Equation (3) through a difference between a first unipolar electrogram and a second unipolar electrogram which are calculated when an electrode contact state of the pseudo electrode is generally good.

$$V_{(E1-E2)\_2} = V_{E1\_2} - V_{E2\_2} = \frac{1}{32} \sum_{x=493}^{500} \sum_{y=500}^{503} V(x, y) - \frac{1}{56} \sum_{x=471}^{484} \sum_{y=500}^{503} V(x, y) \quad \text{Equation (3)}$$

Figure 15:
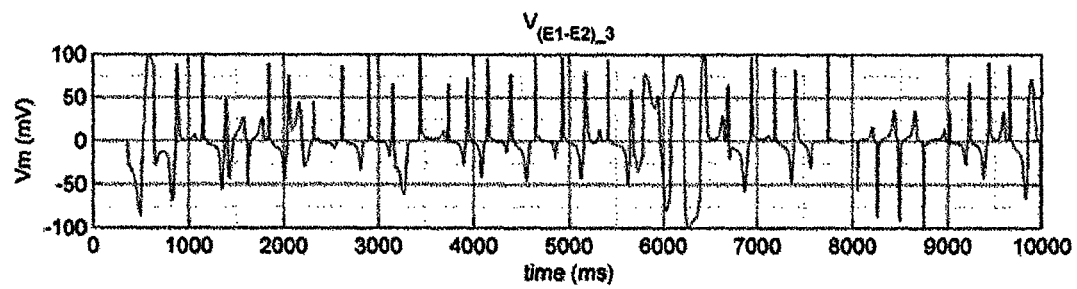
FIG. 15 is a pseudo electrogram generated according to still another exemplary embodiment of the present invention.

FIG. 15 is a pseudo electrogram generated according to still another exemplary embodiment of the present invention. According to the exemplary embodiment of the present invention, the pseudo electrogram generation unit 12 may calculate the pseudo electrogram using Equation (4) through a difference between a first unipolar electrogram and a second unipolar electrogram which are calculated when an electrode contact state of the pseudo electrode is not good.

$$V_{(E1-E2)\_3} = V_{E1\_3} - V_{E2\_3} = \frac{1}{8} \sum_{x=493}^{500} V(x, 500) - \frac{1}{14} \sum_{x=471}^{484} V(x, 500) \quad \text{Equation (4)}$$

The filtering unit 13 may filter only signals in a predetermined frequency range from the pseudo electrogram and output the signals. For example, the filtering unit 13 may filter only signals in a frequency range of 30 Hz to 500 Hz and output the signals, preferably may filter only signals in a frequency range of 30 Hz to 300 Hz and output the signals.

Figure 16:
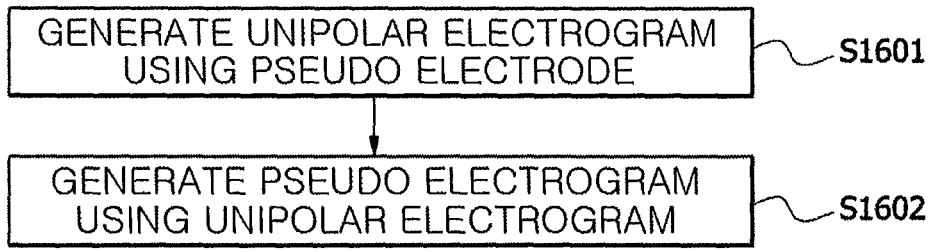
FIG. 16 is a flowchart of a method for generating a pseudo electrogram according to an exemplary embodiment of the present invention.

FIG. 16 is a flowchart of a method for generating a pseudo electrogram according to an exemplary embodiment of the present invention.

A unipolar electrogram is generated using an action potential calculated from the electric physiological model of the heart using a pseudo electrode in which a cross-sectional area is adjusted. The unipolar electrogram may be calculated by the following equation, and unipolar electrograms corresponding to the first electrode 21 and the second electrode 22 of the pseudo electrode, respectively, may be calculated (S1601).

$$V = \frac{S_2}{S_1} \times \sum_{x=x_0}^{x_0+k-1} \sum_{y=y_0}^{y_0+l-1} V(x, y)$$

($S_1$: a cross-sectional area of an electrode, $S_2$: a cross-sectional area of a unit cell, $x_0$: a location of a tip of a pseudo electrode on an x-axis, k: the number of cells occupied by the electrode on the x-axis, $y_0$: a location of a tip of a pseudo electrode on a y-axis, l: the number of cells occupied by the electrode on the y-axis, V: an action potential)

A pseudo electrogram may be generated using a difference between the unipolar electrogram of the first electrode 21 and the unipolar electrogram of the second electrode 22 (S1602).

According to the system and method for generating the pseudo electrogram according to the exemplary embodiments of the present invention, an electrogram for inducing a complex fractionated atrial electrogram can be non-invasively generated using a pseudo electrode. Further, a pseudo electrogram generated using the pseudo electrode can be used for providing location data for performing radiofrequency catheter ablation, predicting electrical physiological activities found in the heart of a patient during surgery, and then predicting and diagnosing a result of the prediction.

Here, the term "unit" refers to software or a hardware component such as a field programmable gate array (FPGA) or an application specific integrated circuit (ASIC), which can perform certain functions. However, the unit is not limited to software or hardware. The unit may be configured in a recording medium which can be addressed or may be configured to execute at least one processor. Examples of the unit may include software components, object-oriented software components, class components, components such as task components, processes, functions, properties, procedures, subroutines, segments in program codes, drivers, firmware, microcode, circuits, data, databases, data structures, tables, arrays, and variables. Components and functions provided from units may be combined into a smaller number of components and units or may be separated into additional components and units. In addition, the components and units may execute at least one CPU in a device.

While the present invention has been described with reference to the exemplary embodiments, it should be understood by those skilled in the art that various changes and modifications may be made herein without departing from the scope of the present invention as defined by the appended claims.

What is claimed is:

1. A system for generating a pseudo electrogram comprising: a computer configured to have
a unipolar electrogram generation unit configured to generate a unipolar electrogram according to an action potential calculated from an electric physiological model of the heart using a pseudo electrode in which a cross-sectional area is adjusted,
the cross-sectional area of the pseudo electrode is set to increase in accordance with electrode contact states of the pseudo electrode,
the electrode contact states of the pseudo electrode are classified into three states of a good state, a normal state, and a non-good state,
the cross-sectional area of the pseudo electrode in the normal state is four times the cross-sectional area of the pseudo electrode in the non-good state, and
the cross-sectional area of the pseudo electrode in the good state is twice the cross-sectional area of the pseudo electrode in the normal state; and
a pseudo electrogram generation unit configured to generate a pseudo electrogram using the unipolar electrogram, the pseudo electrode comprises a first electrode and a second electrode,
the unipolar electrogram generation unit generates the unipolar electrogram according to the following equation $$V = \frac{S_2}{S_1} \times \sum_{x=x_0}^{x_0+k-1} \sum_{y=y_0}^{y_0+l-1} V(x, y)$$

wherein
$S_1$: the cross-sectional area of the pseudo electrode,
$S_2$: a cross-sectional area of a unit cell,
$x_0$: a location of a tip of the pseudo electrode on an x-axis,
k: the number of cells occupied by the electrode on the x-axis,
$y_0$: a location of a tip of the pseudo electrode on a y-axis,
l: the number of cells occupied by the electrode on the y-axis,
V(x,y): the action potential being a unipolar potential for the tip of the pseudo electrode at the location on the x-axis and the y-axis.

2. The system of claim 1 wherein the pseudo electrogram generation unit calculates the pseudo electrogram using a difference between a unipolar electrogram of the first electrode and a unipolar electrogram of the second electrode.

3. The system of claim 1 further comprising a filtering unit configured to filter only a signal in a predetermined frequency range from the pseudo electrogram.

4. The system of claim 3 wherein the filtering unit filters only a signal in a frequency range of 30 Hz to 300 Hz.

5. A method of generating a pseudo electrogram using a computer comprising the steps of:
generating a unipolar electrogram according to an action potential calculated from an electric physiological model of the heart using a pseudo electrode in which a cross-sectional area is adjusted, a cross-sectional area of the pseudo electrode is set to increase in accordance with electrode contact states of the pseudo electrode,
the electrode contact states of the pseudo electrode are classified into three states of a good state, a normal state, and a non-good state,
the cross-sectional area of the pseudo electrode in the normal state is four times the cross-sectional area of the pseudo electrode in the non-good state, and
the cross-sectional area of the pseudo electrode in the good state is twice the cross-sectional area of the pseudo electrode in the normal state; and
generating a pseudo electrogram using the unipolar electrogram, the pseudo electrode comprises a first electrode and a second electrode,
wherein the generating of the unipolar electrogram generates the unipolar electrogram according to the following equation $$V = \frac{S_2}{S_1} \times \sum_{x=x_0}^{x_0+k-1} \sum_{y=y_0}^{y_0+l-1} V(x, y)$$

wherein
$S_1$: the cross-sectional area of the pseudo electrode,
$S_2$: a cross-sectional area of a unit cell,
$x_0$: a location of a tip of the pseudo electrode on an x-axis,
k: the number of cells occupied by the electrode on the x-axis,
$y_0$: a location of a tip of the pseudo electrode on a y-axis,
l: the number of cells occupied by the electrode on the y-axis, V(x,y): the action potential being a unipolar potential for the tip of the pseudo electrode at the location on the x-axis and the y-axis.

6. The method of claim 5 wherein the generating of the pseudo electrogram calculates the pseudo electrogram using a difference between a unipolar electrogram of a first electrode and a unipolar electrogram of a second electrode.

* * * * *